United States Patent
Hu et al.

(10) Patent No.: US 6,370,217 B1
(45) Date of Patent: *Apr. 9, 2002

(54) VOLUMETRIC COMPUTED TOMOGRAPHY SYSTEM FOR CARDIAC IMAGING

(75) Inventors: Hui Hu, Waukesha; Jiang Hsieh, Brookfield; Stanley H. Fox, Brookfield; Kishore C. Acharya, Brookfield; Hui David He; Yi Sun, both of Waukesha, all of WI (US)

(73) Assignee: General Electric Company, Schenectady, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/307,400

(22) Filed: May 7, 1999

(51) Int. Cl.[7] ................................. A61B 6/00
(52) U.S. Cl. ................. 378/8; 378/9; 378/95; 378/98.8
(58) Field of Search ................. 378/8, 9, 95, 98.8

(56) References Cited

U.S. PATENT DOCUMENTS

| | | | |
|---|---|---|---|
| 3,952,201 A | | 4/1976 | Hounsfield |
| 4,182,311 A | | 1/1980 | Seppi et al. |
| 4,530,109 A | | 7/1985 | Klausz |
| 4,641,328 A | | 2/1987 | Fujise |
| 4,994,965 A | | 2/1991 | Crawford et al. |
| 5,271,055 A | * | 12/1993 | Hsieh et al. ............ 378/95 |
| 5,280,428 A | * | 1/1994 | Wu et al. |
| 5,533,085 A | | 7/1996 | Sheehan et al. |
| 5,544,212 A | | 8/1996 | Heuscher |
| 5,602,891 A | | 2/1997 | Pearlman |
| 5,692,507 A | * | 12/1997 | Seppi et al. |
| 5,751,782 A | | 5/1998 | Yoshitome |
| 5,832,051 A | | 11/1998 | Lutz |
| 6,154,516 A | | 11/2000 | Heuscher et al. |
| 6,301,324 B1 | * | 10/2001 | Pearson, Jr. et al. ......... 378/15 |

FOREIGN PATENT DOCUMENTS

| | | |
|---|---|---|
| EP | 0 370 341 A2 | 5/1990 |
| EP | 1 013 225 A1 | 6/2000 |
| EP | 1 050 272 A1 | 11/2000 |
| EP | 1 072 224 A2 | 1/2001 |
| EP | 1 088 517 A1 | 4/2001 |
| EP | 1 090 586 A2 | 4/2001 |
| WO | WO 00/30539 | 6/2000 |

OTHER PUBLICATIONS

Carl Crawford and Kevin King, "Computed Tomography Scanning with Simultaneous Patient Translation," Med. Phys. 17 (6), Nov./Dec. 1990, pp. 967–982.

Spraggins et al., "Retrospective Cardiac Gating Requiring No Physiological Monitoring," undated, document No. XP000079445, p. 104.

Woodhouse et al., "Coronary Arteries: Retrospective Cardiac Gating Technique to Reduce Cardiac Motion Artifact at Spiral CT," Radiology, Aug., 1997, pp. 566–569.

* cited by examiner

Primary Examiner—David V. Bruce
Assistant Examiner—Pamela R. Hobden
(74) Attorney, Agent, or Firm—Carl B. Horton, Esq.; Armstrong Teasdale LLP

(57) ABSTRACT

The present invention, in one form is an imaging system for generating images of an entire object. In one embodiment, a physiological cycle unit is used to determine the cycle of the moving object. By altering the rotational speed of an x-ray source as a function of the object cycle, segments of projection data are collected for each selected phase of the object during each rotation. After completing a plurality of rotations, the segments of projection data are combined and a cross-sectional image of the selected phase of the object is generated. As a result, minimizing motion artifacts.

29 Claims, 2 Drawing Sheets

VOLUMETRIC COMPUTED TOMOGRAPHY SYSTEM FOR CARDIAC IMAGING

BACKGROUND OF THE INVENTION

This invention relates generally to computed tomography (CT) imaging and more particularly, to generating images of a moving object.

In at least one known CT system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In at least one known type of imaging system, commonly known as a computer tomography (CT) system, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles during one revolution of the x-ray source and detector. In an axial scan, the projection data is processed to construct an image that corresponds to a two dimensional slice taken through the object.

One method for reconstructing an image from a set of projection data is referred to in the art as the filtered backprojection technique. This process converts the attenuation measurements from a scan into integers called "CT numbers" or "Hounsfield unit", which are used to control the brightness of a corresponding pixel on a cathode ray tube display.

To reduce the total scan time required for multiple slices, a "helical" scan may be performed. To perform a "helical" scan, the patient is moved while the data for the prescribed number of slices is acquired. Such a system generates a single helix from a one fan beam helical scan. The helix mapped out by the fan beam yields projection data from which images in each prescribed slice may be reconstructed. In addition to reduced scanning time, helical scanning provides other advantages such as improved image quality and better control of contrast.

In helical scanning, and as explained above, only one view of data is collected at each slice location. To reconstruct an image of a slice, the other view data for the slice is generated based on the data collected for other views. Helical reconstruction algorithms are known, and described, for example, in C. Crawford and K. King, "Computed Tomography Scanning with Simultaneous Patient Translation," Med. Phys. 17(6), November/December 1990.

In order to generate images of a rapidly moving object, such as a heart, known imaging systems have minimized motion artifacts, caused by the movement of the heart, by utilizing a high rotational speed gantry or by incorporating electron beam technology. However, the high speed gantry system significantly increases the force applied to the x-ray source and the detector affecting performance of the system. The electron beam technology requires a very complex design that significantly increases the cost of the scanner. As a result, few system are capable of generating images of a moving heart without generating images containing significant motion artifacts.

To generate images of a moving object, it is desirable to provide an imaging system which gathers segments of projection data of a selected phase of the object so that by combining the segments motion artifacts are minimized. It would also be desirable to provide such a system which generates a cross-sectional image of the entire object for a selected phase of the object.

BRIEF SUMMARY OF THE INVENTION

These and other objects may be attained by a CT imaging system that generates images of an entire object of interest using segments of projection data collected from a plurality of projection angles for a selected phase of the object. In accordance with one embodiment of the present invention, the imaging system includes at least one rotating x-ray source and at least one detector array. A physiological cycle unit, or circuit, is utilized to generate a physiological cycle signal of the object. The cycle signal represents the time period of each cycle of the object including a plurality of phases. To generate an image of the object for a selected phase, an operator selects at least one phase of the object. For each selected phase of the object, at least one segment of projection data is collected during each rotation of each x-ray source.

More specifically, each segment of projection data is generated, or collected, by emitting an x-ray beam toward an x-ray detector array for a determined imaging temporal period for each selected phase during each rotation. Particularly, as each x-ray source is rotated, an x-ray beam is emitted for the determined imaging temporal period. As a result, a segment of projection data is collected via each detector array. Each segment represents a small range of angular positions. By altering a rotational speed of each x-ray source, segments of projection data are collected from different projection angles as each x-ray source is rotated. More particularly, the rotational speed of each x-ray source is altered so that each segment of projection data for each selected phase of the object is collected from a different projection angle, or range of projection angles. By completing a plurality of rotations of each x-ray source, projection data is collected for a projection angle range of (180 degrees plus a fan angle).

To generate an image of the selected phase of the object, the segments of projection data collected from the different projection angles are combined. More specifically, the collected segments for a selected phase of the object are combined into a set of projection data for the selected phase. The projection data set is then used to reconstruct a cross-sectional image of the object for the selected phase.

In alternative embodiments, the imaging system collects segments of projection data for a plurality of phases of the object during each rotation of each x-ray source. More specifically, after selecting a plurality of phases, at least one segment of projection data is collected for each selected phase of the object during each rotation of each x-ray source.

The above described imaging system generates images of a moving object by gathering segments of projection data for a selected phase of the object so that motion artifacts are minimized. In addition, the imaging system generates cross-sectional images of the entire object for each selected phase of the object.

DETAILED DESCRIPTION OF THE INVENTION

Figure 1:
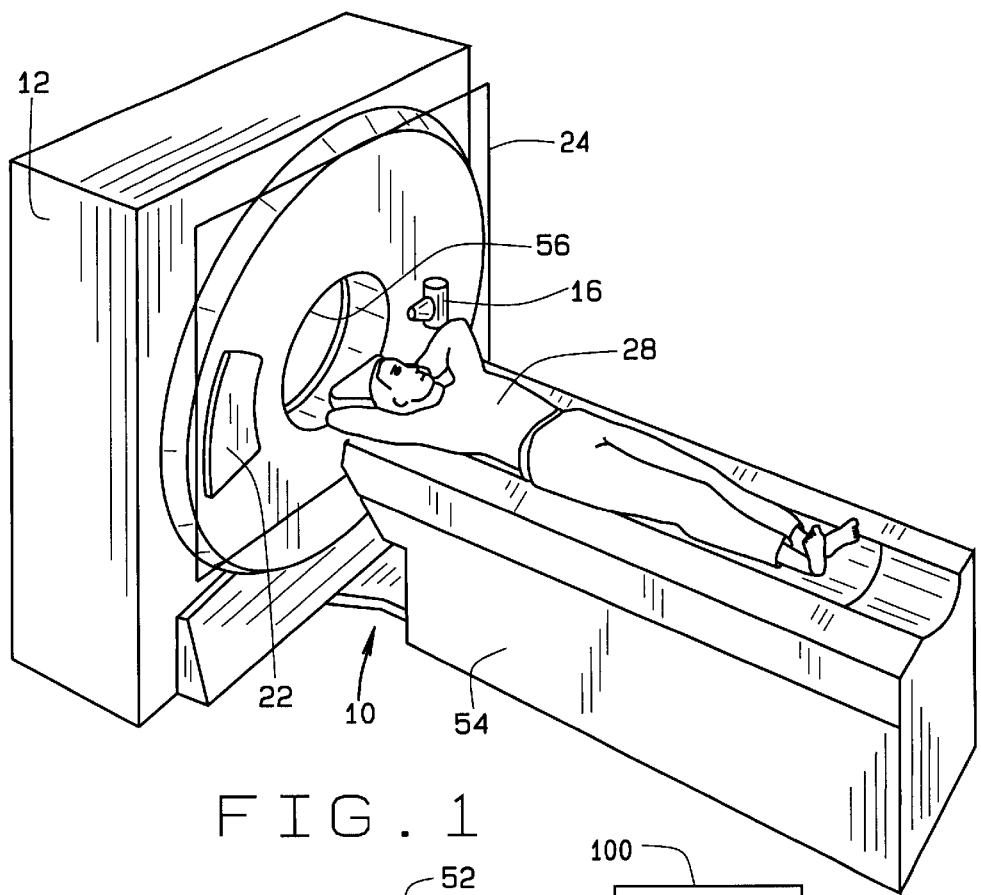
FIG. 1 is a pictorial view of a CT imaging system.
Figure 2:
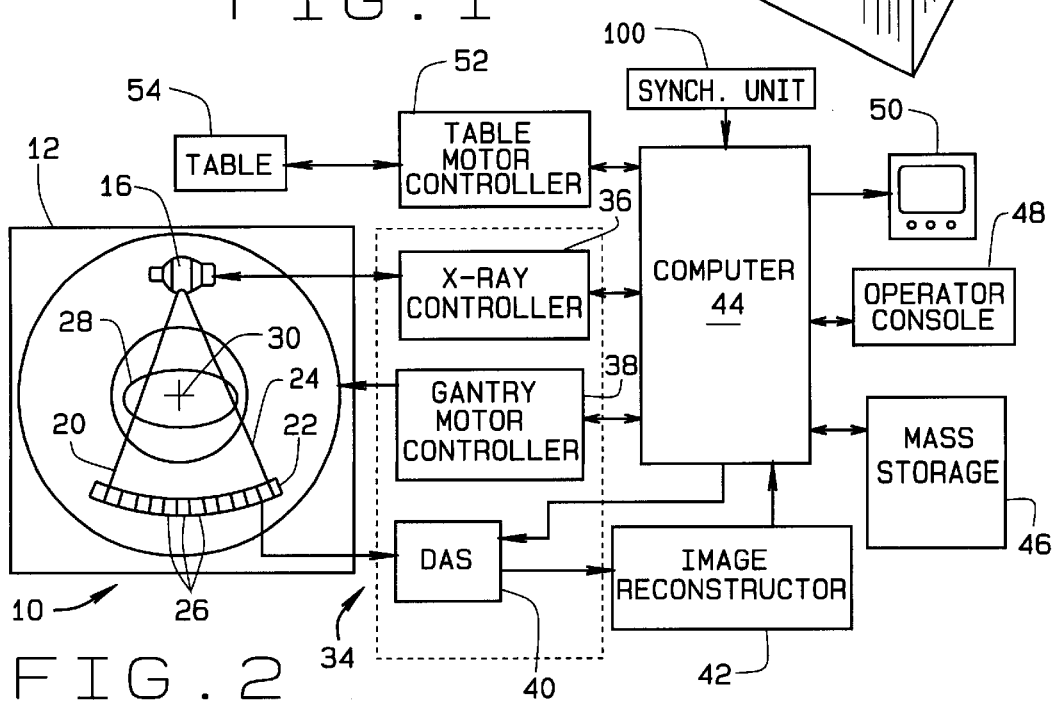
FIG. 2 is a block schematic diagram of the system illustrated in FIG. 1.

Referring to FIGS. 1 and 2, an imaging system 10 is shown as a "third generation" computed tomography (CT) imaging system including a gantry 12 having at least one rotating x-ray source 16 that projects from a focal spot 18 a beam of x-rays 20 toward a detector array 22. X-ray beams 20 extend from source 16 along a beam plane 24. Beam plane 24, generally referred to as the "fan beam plane", contains the centerline of focal spot 18 and the centerline of beam 20 of each source 16. Each x-ray beam 20 is collimated by a collimator (not shown) to lie within in an X-Y plane of a Cartesian coordinate system and generally referred to as an "imaging plane". Each detector array 22 is formed by an array of detector elements 26 which together sense the projected x-rays that pass through a medical patient 28. Detector array 22 may be a single slice detector or a multislice detector. Each detector element 26 produces an electrical signal that represents the intensity of an impinging x-ray beam and hence the attenuation of the beam as it passes through patient 28. During a scan to acquire x-ray projection data, gantry 12 and the components mounted thereon rotate about a center of rotation, or iso-center, 30.

Rotation of gantry 12 and the operation of each x-ray source 16 are governed by a control mechanism 34 of CT system 10. Control mechanism 34 includes an x-ray controller 36 that provides power and timing signals to each x-ray source 16 and a gantry motor controller 38 that controls the rotational speed and position of gantry 12. More specifically, altering the signals supplied to x-ray controller 36 determines when and for how long x-ray beam 20 is emitted from each x-ray source 16. Similarly, the rotational speed of gantry 12 is determined, or altered, by supplying the appropriate signals to gantry motor controller 38. A data acquisition system (DAS) 40 in control mechanism 34 samples analog data from detector elements 26 and converts the data to digital signals for subsequent processing. A sampling rate of DAS 40 is adjustable, or variable, so that the rate at which the data supplied from elements 26 may be increased or decreased. An image reconstructor 42 receives sampled and digitized x-ray data from DAS 40 and performs high speed image reconstruction. The reconstructed image is applied as an input to a computer 44 which stores the image in a mass storage device 46.

Computer 44 also receives commands and scanning parameters from an operator via console 48 that has a keyboard. An associated cathode ray tube display 50 allows the operator to observe the reconstructed image and other data from computer 44. The operator supplied commands and parameters are used by computer 44 to provide control signals and information to DAS 40, x-ray controller 36 and gantry motor controller 38. In addition, computer 44 operates a table motor controller 52 which controls a motorized table 54 to position patient 28 in gantry 12. Particularly, table 54 moves portions of patient 28 through a gantry opening 56.

In one embodiment, system 10 includes a synchronization unit, or circuit 100 to identify or determine, a physiological cycle of the object, i.e., a heart. More specifically and in one embodiment, circuit 100 is coupled to computer 44 and generates a physiological cycle signal representative of the heart including a plurality of phases of the object, e.g., a systole and a diastole phases. System 10 utilizes the physiological signal to synchronize the timing of the emission of x-ray beam 16, the collection rate of projection data segments using DAS 40, and the rotational speed of gantry 12 so that an image of the heart is generated for the determined, or selected, phase of a heart cycle.

Figure 3:
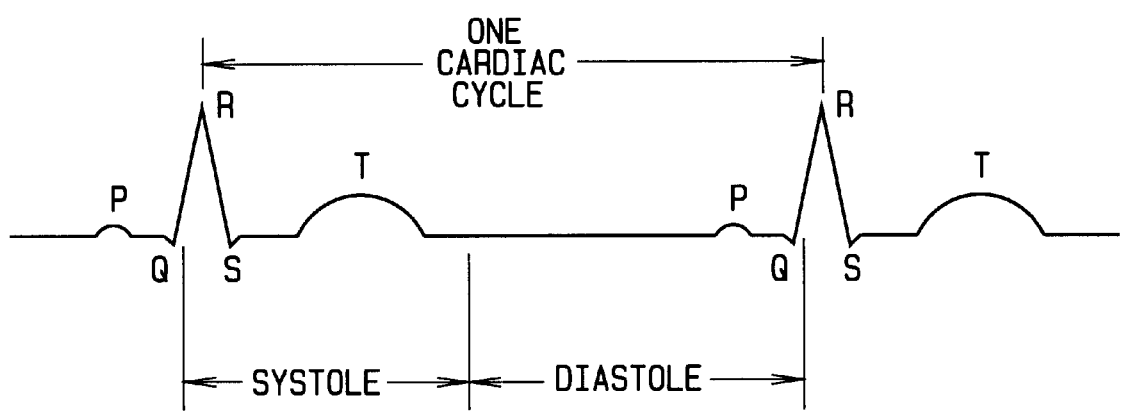
FIG. 3 is a illustration of a physiological cycle of a heart.

More specifically and in one embodiment, circuit 100 measures, or detects, the electrical activity of the heart of patient 28 to identify or determine the cardiac phase signal for each cycle of a patient's heart. In one embodiment, an output signal of at least one electrode (not shown) attached to patient 28 is supplied to an electronic amplifier (not shown) within circuit 100 which generates the cardiac phase signal. For example, and as shown in FIG. 3, the cardiac cycle signal waveform illustrates one cardiac cycle including the systole condition, or phase, and a diastole condition or phase, of the heart. The portion of the signal which is labeled Q, R and S is referred to as the QRS complex, in which the R-feature, or R-wave, is the most prominent, highest amplitude, feature of the entire signal. In one embodiment, the cardiac cycle determines the period of each heart cycle and the timing of each phase of the heart. The amount of time required for the heart to complete one cardiac cycle is identified as a cardiac period, w, and typically is defined as beginning with a R-wave and continuing until the occurrence of the next R-wave. In other embodiments, the cardiac cycle signal may be generated by an EKG subsystem or heart monitoring device as known in the art.

In one embodiment, system 10 is configured to generate a volumetric image of an entire object within patient 28, for example a heart (not shown), by collecting at least one portion, or segment, of a projection data set during each rotation of gantry 12. After collecting the entire projection data set, the projection data segments are combined and a reconstruction algorithm is used to generate the volumetric tomographic image of the heart. More specifically and in one embodiment, each segment of projection data is collected for a determined time period, or temporal window for a pre-determined, or operator selected, phase of the heart during rotation of gantry 12. After completing a plurality rotations of each x-ray source 16, a reconstruction algorithm stored within image reconstructor 42 combines the projection data segments and generates a volumetric cross-sectional image of the heart for the determined phase.

More specifically and in one embodiment, system 10 utilizes circuit 100 to identify the physiological cycle of the object, i.e., a heart and a plurality of phases of the heart. An operator then selects at least one phase of the heart to image using the physiological signal. For example, the operator utilizes console 48 to select a systole phase of the heart. For each selected phase of the object, at least one segment of projection data is collected during each rotation of each x-ray source 16.

More specifically, each segment of projection data, in one embodiment, is generated, or collected, by emitting an x-ray beam 20 toward an x-ray detector array 22 for a determined imaging temporal period, $R_t$, during each selected phase. Particularly, during each rotation of each x-ray source 16, an x-ray beam 20 is emitted for the determined imaging temporal period. The projection data collected via each detector array 22 during the temporal period represents a range of angular positions. Specifically, utilizing the cycle signal supplied from circuit 100, the emission of x-ray beam 16 is limited to the nominal period of Rt at the defined phase of each cycle. More specifically, utilizing the physiological cycle signal, the emission of x-ray beam 16 is turned on and off by altering a signal supplied to x-ray controller 36. In one embodiment, the imaging temporal period is in a range of 10 mS to 50 mS.

The projection data segment acquired from detector array 22 during the emission of x-ray beam 20 represents a small, or limited, portion of angular positions within the time duration of Rt. Particularly, the cycle signal is utilized by DAS 40 to alter the sampling rate of each detector array 22 so that the outputs of elements 26 are sampled only during the period of emission of x-ray beam 20. During each subsequent rotation of each x-ray source 16, a segment of projection data is collected for a different radial, or projection, angle for each selected phase.

In one embodiment, a rotational speed of each x-ray source 16 is altered, or determined, so that at least one segment of projection data is collected during each rotation of each x-ray source 16. More specifically and in one embodiment, the rotational speed of each x-ray source 16 is altered so that each segment of projection data for each selected phase of the object is collected from a different projection angle, or range of projection angles. In one embodiment, by altering the signals supplied to gantry motor controller 38, each x-ray source 16 is rotated a plurality of rotations so that projection data is collected for a projection angle range of (180 degrees plus a fan angle). For example, segments of projection data for each selected phase of the heart are collected from a projection angle range of 225 degrees. As a result of each segment representing an approximate 18 degree change in projection angle, a complete set of projection data may be acquired in about 13 to 20 seconds, less than a single breath-holding time, depending upon the imaging requirements.

More particularly and in one embodiment, the rotational speed of each x-ray source 16, in rotations per second, is determined in accordance with:

$$V_G = \frac{1}{(T_C \pm (n * R_t))},$$

where:
 Tc is the cardiac cycle time in seconds;
 n is an integer constant; and
 Rt is the determined imaging temporal period in seconds.
For example, if n equals one, Tc equals 1 second and Rt equals 0.05 seconds, the rotating speed of each x-ray source 16 is approximately 1.05 revolutions per second or 0.95 revolutions per second. As a result, a complete set of projection data segments is collected in 13 to 20 seconds depending on image quality requirements.

In one embodiment, the time required to collect a complete set of projection data may be reduced by altering the rotational speed of each x-ray source 16 in accordance with:

$$V_G = \left(\frac{180 + \frac{\gamma}{n}}{180 * w}\right), \text{ (in rotations per second)}$$

where:
 w is the period of a physiological cycle (in seconds),
 γ is the projection angle range for a complete projection data set (in degrees), and
 n is a selected integer number of cycles to collect a complete projection data set.

In an alternative embodiment, the time required to collect a complete set of projection data may be reduced by altering the rotational speed of each x-ray source 16 in accordance with:

$$V_G = \left(\frac{360 + \frac{\gamma}{n}}{360 * w}\right), \text{ (in rotations per second)}$$

where:
 w is the period of a physiological cycle (in seconds),
 γ is the projection angle range for a complete projection data set (in degrees), and
 n is a selected integer number of cycles to collect a complete projection data set. Using this method of altering the rotational speed of each x-ray source 16, the data span within each physiological cycle is improved from $(\gamma/(360*V_G))$ seconds to $(\gamma/(360*V_G*n))$ seconds, and improvement of a factor of n. For example, utilizing this method in a single slice CINE CT mode, a projection data set representing one slice of projection data is collected in (n*t) seconds. The rotation speed of each x-ray source 16 may also be altered in accordance with this method in a Helical mode to obtain projection data to generate a volumetric data in one scan of the object.

More specifically and.in one embodiment, in a multi-slice helical CT scan mode, projection data is collected using a relatively fast table speed. Using multiple rows of each detector array 22, fast volume coverage is achieved. Particularly, z resolution degradation is minimized when the speed of table 54, as determined by table controller 52, is altered so that the table speed, s, is determined in accordance with:

$$(i*d)/w,$$

where,
 d is a detector row spacing of detector array 22, and
 i is an integer.
For example, where d equals 5 mm, w equals 0.8 seconds and i equals 3, the z resolution degradation is minimized when the speed of table 54 is 18.95 mm/second.

In one embodiment, after collecting the segments of projection data, the segments are combined into a projection data set and a cross-sectional image of the object is generated from the projection data set. More specifically, a projection data set is generated for each selected phase of the object by combining the projection data segments collected for the selected phase. For example, where a first selected phase is a systole phase of the heart, a first projection data set is generated by combining the projection data segments collected from the plurality of projection angles for the systole phase of the heart. In a similar manner, a separate projection data set is then generated for each additional selected phase of the object. For example, a second projection data set may be generated by combining the projection data segments collected from the diastole phase of the heart.

In one embodiment, the projection data set generated for a selected phase is utilized to generate a cross-sectional image of the entire object. More specifically and in one embodiment, a cross-sectional, or volumetric tomographic, image is generated, using a reconstruction algorithm stored in image reconstructor 42, for each selected phase of the object. Each projection data set is used to generate a separate cross-sectional image of the entire object for each selected phase of the object. For example, using system 10 in a single cardiac phase mode, where the operator selects only a first phase to generate an image, the first set of projection data is used to generate a cross-sectional image of the entire heart in the first phase.

In one embodiment, circuit 100 also monitors each physiological cycle to determine if an arrhythmic, or abnormal, condition exists to determine whether the segments of projection collected are valid. More specifically and in one embodiment, circuit 100 determines an average cycle period by measuring the time period of a selected number of cycles. For each completed cycle of the object, circuit 100 compares the average cycle period to a cycle period for the completed cycle. If the completed cycle period exceeds the average cycle period plus or minus a tolerance, the completed cycle is identified as an arrhythmic cycle. The arrhythmic cycle causes the collected segments of projection data to not represent the selected phase. In one embodiment, the segments collected during the arrhythmic cycle are not used and replacement segments of projection data are collected.

In an alternative embodiment defined as a multi-phase cardiac mode, projection data sets are generated from a plurality of selected phases of the object during each rotation of each x-ray source 16. More specifically, segments of projection data are collected as described above except that each x-ray source 16 is turned on a plurality of times during each rotation so that segments of projection data are collected from plurality of selected phases of the object during each rotation. In another embodiment of the multi-phase cardiac mode, segments of projection data are collected from a plurality of segments for each selected phase of the object during each rotation of each x-ray source 16.

In the multi-phase cardiac imaging mode, projection data is collected for a plurality of selected cardiac phases during each rotation of gantry 12 so that separate images are generated for each selected cardiac phase. More specifically and in one embodiment, the multi-phase cardiac imaging mode operates similar to the single phase cardiac imaging mode except separate images are generated for a plurality of phases of the heart. Initially, the user determines, or selects, a plurality of cardiac phases to be imaged. By altering the amount of time between each selected phase, images of different phases of the heart may be generated, for example for a systolic and a diastolic phase. After selecting a plurality of phases, gantry 12 is rotated as described above. For each rotation of gantry 12, x-ray beam 20 is emitted from source 14 toward detector array 22 for each selected cardiac phase and a segment of projection data is collected by detector array 22 for each selected cardiac phase. Particularly and as described above, utilizing circuit 100, the rotational speed of gantry 12 and the sampling rate of DAS 40 are altered so that projection data is collected for the plurality of cardiac phases. After collecting a complete set of projection for each cardiac phase as described above, the reconstruction algorithm generates a volumetric image of each selected phase of the heart.

Utilizing the above described mode and by increasing the rotational speed of gantry 12, either the image temporal resolution or the total scan time for a given organ coverage is significantly improved. For example, if gantry 12 is rotated so that gantry 12 completes two complete rotation during a single cardiac cycle, the temporal resolution is improved by 50% versus a system completing one rotation per cardiac cycle.

In yet another embodiment of the present invention, an image of cardiac wall motion may be generated by acquiring multiple segments of projection data during a short period of time, for example four seconds. In an alternative embodiment, continuous segments of projection data is collected and the data is rebinned for different phases of a cardiac cycle.

The above described imaging system generates images of a moving object by gathering segments of projection data for a selected phase of the object so that motion artifacts are minimized. In addition, the imaging system generates cross-sectional images of the entire object for each selected phase of the object.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. For example, imaging system may be configured as a "fourth generation" system having at least one rotating x-ray source and at least one fixed position detector array. Accordingly, the spirit and scope of the invention are to be limited only by the terms of the appended claims.

What is claimed:

1. A method for generating an image of an object using a computed tomography (CT) imaging system, the imaging system including an x-ray detector array and a rotating x-ray source projecting an x-ray beam, said method comprising:
   identifying a physiological cycle of the object, the cycle comprising a plurality of phases;
   selecting at least one phase of the object;
   collecting at least one segment of projection data for each selected phase of the object during each rotation of the x-ray source;
   generating a projection data set by combining the projection data segments from more than one cycle of the object; and
   generating a cross-sectional image of the entire object from the projection data set.

2. A method in accordance with claim 1 wherein generating a projection data set by combining the projection data segments comprises generating a projection data set for each selected phase of the object by combining the projection data segments collected for the selected phase.

3. A method in accordance with claim 1 wherein collecting at least one segment of projection data for each selected phase of the object during each rotation of the x-ray source comprises:
   rotating the x-ray source a plurality of rotations; and
   emitting an x-ray beam from the x-ray source towards the x-ray detector array from a plurality of projection angles.

4. A method in accordance with claim 3 wherein collecting at least one segment of projection data for each selected phase of the object during each rotation of the x-ray source further comprises collecting each segment of projection data for the selected phase from a different projection angle.

5. A method for generating an image of an object using a computed tomography (CT) imaging system, the imaging system including an x-ray detector array and a rotating x-ray source projecting an x-ray beam, said method comprising:
   identifying a physiological cycle of the object, the cycle comprising a plurality of phases;
   selecting at least one phase of the object;
   collecting at least one segment of projection data for each selected phase of the object during each rotation of the x-ray source;
   generating a projection data set by combining the projection data segments; and generating a cross-sectional image of the entire object from the projection data set;

wherein collecting at least one segment of projection data for each selected phase of the object during each rotation of the x-ray source further comprises collecting each set of projection data for the selected phase from a different projection angle;

and further wherein collecting each set of projection data for the selected phase from a different projection angle comprises altering a rotation speed of the x-ray source.

6. A method in accordance with claim 5 wherein emitting an x-ray beam from the x-ray source towards an x-ray detector from a plurality of projection angles comprises emitting an x-ray beam from the x-ray source for a determined imaging temporal period.

7. A method for generating an image of an object using a computed tomography (CT) imaging system, the imaging system including an x-ray detector array and at least one rotating x-ray source projecting an x-ray beam, said method comprising:

identifying a physiological cycle of the object, the cycle comprising a plurality of phases;

selecting at least one phase of the object;

collecting at least one segment of projection data for each selected phase of the object during each rotation of the x-ray source;

generating a projection data set by combining the projection data segments; and generating a cross-sectional image of the entire object from the projection data set;

wherein collecting at least one segment of projection data for each selected phase of the object during each rotation of the x-ray source further comprises collecting each set of projection data for the selected phase from a different projection angle;

wherein collecting each set of projection data for the selected phase from a different projection angle comprises altering a rotation speed of the x-ray source;

wherein emitting an x-ray beam from the x-ray source towards an x-ray detector from a plurality of projection angles comprises emitting an x-ray beam from the x-ray source for a determined imaging temporal period; and wherein the rotational speed of each x-ray source is determined in accordance with:

$$V_G = \frac{1}{(T_c \pm (n * R_t))} \text{ (in revolutions per second)},$$

where:

$T_c$ is the cardiac cycle time in seconds;

n is an integer constant; and $R_t$ is the determined imaging temporal period in seconds.

8. A method for generating an image of an object using a computed tomography (CT) imaging system, the imaging system including an x-ray detector array and at least one rotating x-ray source projecting an x-ray beam, said method comprising:

identifying a physiological cycle of the object, the cycle comprising a plurality of phases;

selecting at least one phase of the object;

collecting at least one segment of projection data for each selected phase of the object during each rotation of the x-ray source;

generating a projection data set by combining the projection data segments; and generating a cross-sectional image of the entire object from the projection data set;

wherein collecting at least one segment of projection data for each selected phase of the object during each rotation of the x-ray source further comprises collecting each set of projection data for the selected phase from a different projection angle;

wherein collecting each set of projection data for the selected phase from a different projection angle comprises altering a rotation speed of the x-ray source;

wherein emitting an x-ray beam from the x-ray source towards an x-ray detector from a plurality of projection angles comprises emitting an x-ray beam from the x-ray source for a determined imaging temporal period; and wherein collecting at least one segment of projection data for each cycle of the object comprises altering the rotational speed of the x-ray source in accordance with:

$$V_G = \left(\frac{180 + \frac{\gamma}{n}}{180 * w}\right), \text{ (in rotations per second)}$$

where:

w is a period of a physiological cycle (in seconds),

γ is a projection angle range for a complete projection data set (in degrees), and n is a selected integer number of cycles to collect a complete projection data set.

9. A method for generating an image of an object using a computed tomography (CT) imaging system, the imaging system including an x-ray detector array and at least one rotating x-ray source projecting an x-ray beam, said method comprising:

identifying a physiological cycle of the object, the cycle comprising a plurality of phases;

selecting at least one phase of the object;

collecting at least one segment of projection data for each selected phase of the object during each rotation of the x-ray source;

generating a projection data set by combining the projection data segments; and generating a cross-sectional image of the entire object from the projection data set;

wherein collecting at least one segment of projection data for each selected phase of the object during each rotation of the x-ray source further comprises collecting each set of projection data for the selected phase from a different projection angle;

wherein collecting each set of projection data for the selected phase from a different projection angle comprises altering a rotation speed of the x-ray source;

wherein emitting an x-ray beam from the x-ray source towards an x-ray detector from a plurality of projection angles comprises emitting an x-ray beam from the x-ray source for a determined imaging temporal period; and wherein collecting at least one segment of projection data for each cycle of the object comprises altering the rotational speed of the x-ray source in accordance with:

$$V_G = \left(\frac{180 + \frac{\gamma}{n}}{180 * w}\right), \text{ (in rotations per second)}$$

where:
w is a period of a physiological cycle (in seconds),
γ is a projection angle range for a complete projection data set (in degrees), and
n is a selected number of cycles to collect a complete projection data set.

10. A computed tomography (CT) imaging system for generating an image of an object, said imaging system including an x-ray detector array and a rotating x-ray source projecting an x-ray beam, said imaging system configured to:
identify a physiological cycle of the object, the cycle comprising a plurality of phases;
accept an input from an operator specifying at least one phase of the object;
collect at least one segment of projection data for each selected phase of the object during each rotation of the x-ray source;
generate a projection data set by combining the projection data segments; and
generate a cross-sectional image of the entire object from said projection data set;
wherein to collect at least one segment of projection data for each cycle of the object, said imaging system configured to alter the rotational speed of said x-ray source in accordance with:

$$V_G = \left(\frac{180 + \frac{\gamma}{n}}{180 * w}\right), \text{ (in rotations per second)}$$

where:
w is a period of a physiological cycle (in seconds),
γ is a projection angle range for a complete projection data set (in degrees), and
n is a selected integer number of cycles to collect a complete projection data set.

11. A method in accordance with claim 1 wherein selecting at least one phase of the object comprises:
selecting a first selected phase of the object; and
selecting a second selected phase of the object.

12. A method in accordance with claim 1 wherein identifying a physiological cycle of the object comprises identifying a physiological cycle of a heart including a systolic phase and a diastolic phase.

13. A method in accordance with claim 1 wherein identifying a physiological cycle of the object comprises identifying a physiological cycle of a respiratory system.

14. A method in accordance with claim 1 wherein generating a projection data set by combining the projection data segments comprises:
rotating the x-ray source a plurality of projection angles;
collecting projection data for a plurality of projection angles using the detector array; and
rebinning the projection data for each selected phase of the object.

15. A method in accordance with claim 1 wherein collecting at least one segment of projection data for each selected phase of the object during each rotation of the x-ray source comprises:

detecting an arrhythmic cycle of the object; and
collecting replacement projection data for the projection data collected during the arrhythmic cycle.

16. A computed tomography (CT) imaging system for generating an imaging of an object, said imaging system including an x-ray detector array and a rotating x-ray source projecting an x-ray beam, said imaging system configured to:
identify a physiological cycle of the object, the cycle comprising a plurality of phases;
accept an input from an operator specifying at least one phase of the object;
collect at least one segment of projection data for each selected phase of the object during each rotation of the x-ray source;
generate a projection data set by combining said projection data segments from more than one cycle of the object; and
generate a cross-sectional image of the entire object from said projection data set.

17. An imaging system in accordance with claim 16 wherein to generate a projection data set by combining said projectionsegments, said imaging system configured to generate said projection data set for each said selected phase of the object by combining said projection data segments collected for the selected phase.

18. An imaging system in accordance with claim 16 wherein to collect at least one segment of projection data for each selected phase of the object during each rotation of said x-ray source, said imaging system configured to:
rotate said x-ray a plurality of rotations; and
emit an x-ray beam from said x-ray source toward said x-ray detector array from a plurality of projection angles.

19. An imaging system in accordance with claim 18 wherein to collect at least one segment of projection data from each selected phase of the object during each rotation of said x-ray source, said imaging system further configured to collect each segment of projection data for the selected phase from a different projection angle.

20. A computed tomography (CT) imaging system for generating an image of an object, said imaging system including an x-ray detector array and a rotating x-ray source projecting an x-ray beam, said imaging system configured to:
identify a physiological cycle of the object, the cycle comprising a plurality of phases;
accept an input from an operator specifying at least one phase of the object;
collect at least one segment of projection data for each selected phase of the object during each rotation of the x-ray source;
generate a projection data set by combining the projection data segments; and
generate a cross-sectional image of the entire object from said projection data set;
wherein to collect at least one segment of projection data for each selected phase of the object during each rotation of said x-ray source, said system is configured to alter a rotational speed of the x-ray source.

21. An imaging system in accordance with claim 20 wherein to emit an x-ray beam from said x-ray source toward said x-ray detector array from a plurality of projection angles, said imaging system configured to emit an x-ray beam from said x-ray source for a determined imaging temporal period.

22. A computed tomography (CT) imaging system for generating an image of an object, said imaging system including an x-ray detector array and a rotating x-ray source projecting an x-ray beam, said imaging system configured to:

identify a physiological cycle of the object, the cycle comprising a plurality of phases;

accept an input from an operator specifying at least one phase of the object;

collect at least one segment of projection data for each selected phase of the object during each rotation of the x-ray source;

generate a projection data set by combining the projection data segments; and generate a cross-sectional image of the entire object from said projection data set;

wherein the rotational speed of said x-ray source is determined in accordance with:

$$V_G = \frac{1}{(T_C \pm (n * R_t))} \text{ (in revolutions per second)},$$

where:

$T_c$ is the cardiac cycle time in seconds;

n is an integer constant; and $R_t$ is said determined imaging temporal period in seconds.

23. A computed tomography (CT) imaging system for generating an image of an object, said imaging system including an x-ray detector array and a rotating x-ray source projecting an x-ray beam, said imaging system configured to:

identify a physiological cycle of the object, the cycle comprising a plurality of phases;

accept an input from an operator specifying at least one phase of the object;

collect at least one segment of projection data for each selected phase of the object during each rotation of the x-ray source;

generate a projection data set by combining the projection data segments; and generate a cross-sectional image of the entire object from said projection data set;

wherein to collect at least one segment of projection data for each cycle of the object, said imaging system configured to alter the rotational speed of said x-ray source in accordance with:

$$V_G = \left(\frac{180 + \frac{\gamma}{n}}{180 * w}\right), \text{ (in rotations per second)}$$

where:

w is a period of a physiological cycle (in seconds),

γ is a projection angle range for a complete projection data set (in degrees), and n is a selected number of cycles to collect a complete projection data set.

24. An imaging system in accordance with claim 16 wherein said rotating x-ray source is a first rotating x-ray source, said x-ray detector array is a first x-ray detector array, and further comprising a second rotating x-ray source and a second detector array, and wherein to collect at least one segment of projection data, said imaging system is configured to collect at least one segment of projection data for each selected phase of the object during each rotation of the first x-ray source.

25. An imaging system in accordance with claim 16 wherein to accept an input from an operator specifying at least one phase of the object, said imaging system configured to:

accept an input from an operator to select a first selected phase of the object; and accept an input from an operator to select a second selected phase of the object.

26. An imaging system in accordance with claim 16 wherein to identify a physiological cycle of the object, said imaging system configured to identify a physiological cycle of a heart comprising a systolic phase and a diastolic phase.

27. An imaging system in accordance with claim 16 wherein to identify a physiological cycle of the object, said imaging system configured to identify a physiological cycle of a respiratory system.

28. An imaging system in accordance with claim 16 wherein to generate a projection data set by combining the projection data segments, said imaging system configured to:

rotate said x-ray source a plurality of projection angles;

collect projection data for a plurality of projection angles using said detector array; and rebin the projection data for each selected phase of the object.

29. An imaging system in accordance with claim 16 wherein to collect at least one segment of projection data for each selected phase of the object during each rotation of said x-ray source, said imaging system configured to:

detect an arrhythmic cycle of the object; and collect replacement projection data for the projection data collected during said arrhythmic cycle.

* * * * *

UNITED STATES PATENT AND TRADEMARK OFFICE
CERTIFICATE OF CORRECTION

PATENT NO. : 6,370,217 B1
DATED : April 9, 2002
INVENTOR(S) : Hu et al.

It is certified that error appears in the above-identified patent and that said Letters Patent is hereby corrected as shown below:

Column 11,
Line 43, delete "integer".

Column 12,
Line 24, delete "projectionsegments" and insert therefor -- projection data segments --.

Signed and Sealed this

Twenty-sixth Day of August, 2003

JAMES E. ROGAN
*Director of the United States Patent and Trademark Office*